(12) United States Patent
Azizian et al.

(10) Patent No.: US 9,622,831 B2
(45) Date of Patent: Apr. 18, 2017

(54) METHOD AND APPARATUS TO PROVIDE UPDATED PATIENT IMAGES DURING ROBOTIC SURGERY

(71) Applicants: Siemens Aktiengesellschaft, Munich (DE); Intuitive Surgical Inc., Sunnyvale, CA (US)

(72) Inventors: Mahdi Azizian, Santa Clara, CA (US); Lutz Blohm, Moehrendorf (DE); Holger Kunze, Bubenreuth (DE); Christine Niebler, Rueckersdorf (DE); Jonathan Sorger, Belmont, CA (US)

(73) Assignees: Siemens Healthcare GmbH, Erlangen (DE); Intuitive Surgical Operations, Inc., Sunnyvale, CA (US)

( * ) Notice: Subject to any disclaimer, the term of this patent is extended or adjusted under 35 U.S.C. 154(b) by 108 days.

(21) Appl. No.: 14/716,963

(22) Filed: May 20, 2015

(65) Prior Publication Data
US 2016/0338797 A1 Nov. 24, 2016

(51) Int. Cl.
*A61B 90/00* (2016.01)
*A61B 34/30* (2016.01)

(52) U.S. Cl.
CPC .............. *A61B 90/37* (2016.02); *A61B 34/30* (2016.02); *A61B 2090/368* (2016.02); *A61B 2090/373* (2016.02); *A61B 2090/374* (2016.02); *A61B 2090/3762* (2016.02)

(58) Field of Classification Search
CPC ... A61B 34/30; A61B 90/37; A61B 2090/373; A61B 2090/374; A61B 2090/368; A61B 2090/3762
See application file for complete search history.

(56) References Cited

U.S. PATENT DOCUMENTS

| | | | |
|---|---|---|---|
| 2001/0025183 A1* | 9/2001 | Shahidi | A61B 90/10 606/130 |
| 2003/0216836 A1* | 11/2003 | Treat | A61B 90/92 700/245 |
| 2004/0128026 A1* | 7/2004 | Harris | B25J 9/1689 700/245 |
| 2006/0142657 A1* | 6/2006 | Quaid | A61N 1/372 600/424 |
| 2010/0274087 A1* | 10/2010 | Diolaiti | A61B 1/00087 600/118 |

(Continued)

*Primary Examiner* — Bo J Peng
(74) *Attorney, Agent, or Firm* — Schiff Hardin LLP

(57) ABSTRACT

In a method and an apparatus to provide updated images during a robotically-implemented surgical procedure, 3D data are obtained of a volume of a patient, which includes anatomy involved in the procedure. The anatomy is segmented from a reconstructed image of the volume. During the procedure, the surgeon applies forces on the anatomy, causing a geometric change of the anatomy. Force sensors in the surgical robot detect these forces, which are supplied to a processor that controls display of the segmented anatomy at a display screen. From the applied forces and the physical properties of the anatomy, the processor calculates the geometric change of the anatomy that has occurred and modifies the appearance and/or position of the displayed segmented anatomy on the display screen in real time during the procedure, so as to visualize the geometric change.

13 Claims, 2 Drawing Sheets

(56) References Cited

U.S. PATENT DOCUMENTS

| | | | |
|---|---|---|---|
| 2011/0077504 A1* | 3/2011 | Fischer | A61B 34/30 600/411 |
| 2011/0201885 A1* | 8/2011 | Okamura | A61B 19/5225 600/109 |
| 2012/0265051 A1* | 10/2012 | Fischer | A61B 10/0241 600/411 |
| 2013/0345718 A1* | 12/2013 | Crawford | A61B 17/025 606/130 |

* cited by examiner

METHOD AND APPARATUS TO PROVIDE UPDATED PATIENT IMAGES DURING ROBOTIC SURGERY

BACKGROUND OF THE INVENTION

Field of the Invention

The present invention concerns imaging systems and procedures used to provide images during the course of a surgical procedure implemented by a robotic manipulator.

Description of the Prior Art

Robotically implemented medical procedures, commonly called robotic surgery, is in widespread use for a variety of medical interventional procedures involving many different organs of a patient. Particularly in the case of abdominal procedures, such as those involving the pancreas or the liver, the organ in question is physically moved or otherwise modified by the robotic manipulator during the course of the procedure. Such changes are designated below as geometric changes to the region or anatomy. Similar changes in the organ or the region of interest also occur at other sites within the patient.

As is well known, commercially available robotic manipulators are operated by a physician (surgeon) to execute a number of physical interactions with one or more organs during the procedure, such as grabbing, cutting, pushing, pulling, etc. It is often the case that the surgical site is resected in order to expose the organ that is being manipulated, but certain types of procedures can also be implemented with only a small incision for introducing an instrument or endoscope.

Typically a computed tomography or magnetic resonance image of the surgical site is obtained as part of a planning procedure. During the actual procedure, an endoscopic image is typically obtained, and the content of such an endoscopic image is thus limited by the field of view of the camera that is used to obtain the endoscopic image. The endoscopic image can include only contents that are within the direct line of sight of the camera and thus only the sides of organs and surrounding tissue that are facing the camera can be seen in such an image.

Although the organ of interest in the planning image can be segmented and then rotated, translated or otherwise changed in known ways at the display screen, the planning image, since it was obtained before the surgical procedure started, will not show changes in the organ itself, such as cutting thereof, that occur during the course of the surgical procedure, and also will not show changes in the position of the organ that may also occur during the course of the procedure.

Known robotic manipulators that are used in surgical procedures are operated from a control console, at which the surgeon is situated. The control console includes a number of manually operated or manipulated elements that the physician operates in the same manner as if the physician were using an instrument at the actual site of the surgery. Thus, for example, if the physician wants to implement a cutting procedure on the organ via the robotic manipulator, a scissors-like control element will be provided at the console. The corresponding cutter of the robotic manipulator is provided with appropriate force sensors, which detect forces at the organ that are applied by the robotic manipulator, and also detect forces on the robotic manipulator that are produced by the organ. This combination of forces provides haptic feedback to the surgeon at the console so that the surgeon operating the scissors-like control element will experience the same cutting force, and resistance of the organ to such a cutting force, that the surgeon would feel if the physician were directly manually operating a cutting element at the surgery site.

The same is true with regard to other types of instruments that are implemented by the robotic manipulator, such as instruments that grab the organ in order to allow the surgeon to then displace all or a portion of the organ in a selected manner.

SUMMARY OF THE INVENTION

An object of the present invention is to provide a surgeon with one or more displayed images during the course of a robotically-implemented surgical procedure that not only show the current state of the anatomy or organ that is the subject of the intervention, but also allow the surgeon, by manipulating the displayed images, to see portions of the anatomy that are not visible in a conventional endoscopic image.

This object is achieved in accordance with the present invention by a method and an apparatus wherein 3D data are obtained of a volume of a patient, which includes anatomy such as a selected organ, which is to be the subject of a robotically-implemented surgical procedure. The anatomy or organ of interest is then segmented from an image of the aforementioned volume that has been reconstructed from the 3D data. The segmentation can be done either manually or by a computerized pattern recognition segmentation algorithm. During the course of the robotically implemented surgical intervention, the surgeon causes one or more forces on the anatomy or organ to occur that cause a modification or displacement of the anatomy or organ (geometric change). These forces are known by being detected by the force sensors that are conventionally present in commercially available robotic manipulators. These forces are supplied to a processor that controls the display of the segmented anatomy or organ at a display screen that is viewed by the surgeon or an assistant during the procedure. The processor calculates the amount of modification or displacement of the anatomy or organ that has occurred as a result of the applied forces and as a result of the physical properties of the anatomy or organ. The processor then automatically modifies the appearance and/or position of the displayed segmented anatomy or organ on the display screen in real time during the procedure, so that the surgeon always has a current visualization of the state of the anatomy or organ as the procedure progresses. Additionally, because the organ or anatomy has been segmented, all conventional operations that can be applied to displayed, segmented anatomy can be implemented by the surgeon during the procedure, such as rotation, translation, etc. For example, if an anterior view of the anatomy or organ is being displayed, the physician can rotate the organ to obtain a posterior view, which would normally not be able to be seen in the conventional endoscopic images that are used during such procedures.

The data representing the physical properties of the anatomy or organ that is the subject of the surgical intervention, which are used in combination with the forces applied by the robotic manipulator in order to computationally determine the resulting modification or displacement of the anatomy or organ, can be obtained from an anatomical atlas. Such an atlas can be compiled for respective anatomy or organs of a general patient population, or can be more specifically matched to a patient population comparable to the patient who is undergoing the procedure. For example, an atlas can be compiled for patients of an age or medical history comparable to that of the patient, patients exhibiting the same pathological condition of the relevant anatomy or organ, etc.

The present invention also encompasses a non-transitory, computer-readable data storage medium that is encoded with programming instructions that, when executed by one or more processors in which the storage medium is loaded, or that have access to the loaded storage medium, cause any or all of the above embodiments of the method according to the invention to be implemented. The storage medium can be loaded into a processor of a central workstation that controls the overall functions performed during the course of a robotically-implemented surface procedure, or the programming instructions can be distributed appropriately among respective processors that individually have responsibility for controlling a subset of the complete suite of functions.

DESCRIPTION OF THE PREFERRED EMBODIMENTS

Figure 1:
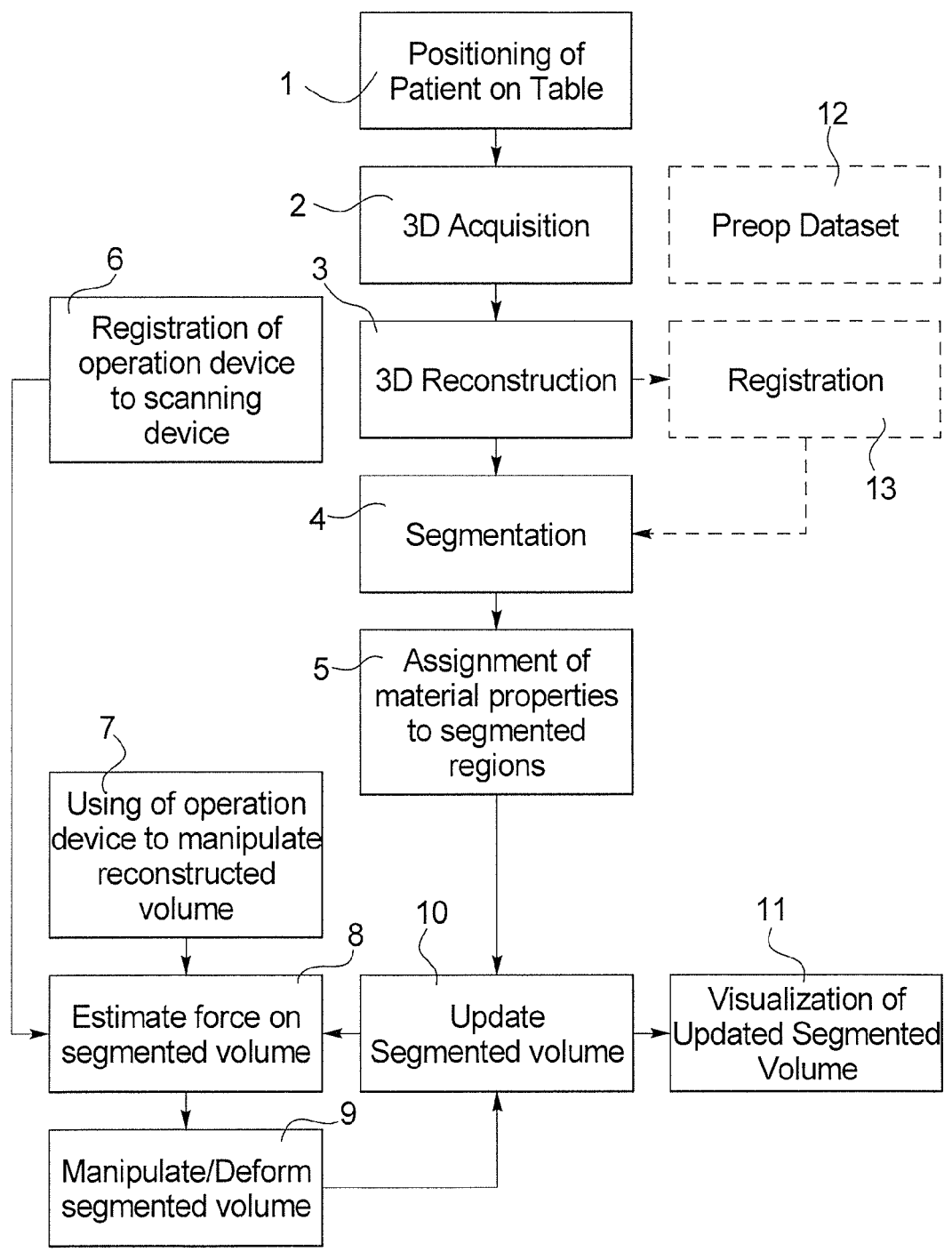
FIG. 1 is a flowchart showing basic steps of the method in accordance with the invention, with optional steps being shown in dashed lines.

As shown in the flowchart of FIG. 1, the method in accordance with the invention begins in step 1 with the positioning of a patient on a table in a surgical venue. The patient is to undergo a robotically-implemented surgical procedure in the operating venue, while on the table.

After the patient has been placed on the table, 3D data are acquired in step 2 from a volume of the patient that includes the anatomy or the organ that is to be the subject of the robotically-manipulated surgical intervention.

In step 3, the acquired 3D data are supplied to a processor, which implements a 3D reconstruction algorithm to generate a 3D image of the volume of the patient represented by the acquired 3D data.

In step 4, the specific anatomy or organ that is the subject of the intervention is segmented from the overall 3D image of the volume. This can be implemented manually, such as by interaction of the surgeon with the displayed image on a screen, with the surgeon using a light pen or cursor to outline the organ or anatomy to be segmented. The segmentation alternatively can be implemented completely automatically, using known pattern recognition-based segmentation algorithms.

An option in accordance with the present invention is to provide, in step 12, a pre-operative data set of the patient, which may be a data set representing one or more medical images of the patient that have been acquired in previous examinations of the patient. Such a pre-operative 3D data set can include any of the known techniques that are used to highlight or enhance selected anatomy or pathological conditions, such as by color coding, contrast agent enhancement, fMRI images in the case of brain surgery being implemented, diffusion-weighted images, etc.

If such a pre-operative data set is optionally provided in step 12, this pre-operative data set is then brought into registration with the aforementioned 3D reconstructed image of the patient on the table in step 13, and the segmentation can then be implemented in order to segment the anatomy or organ from the registered, pre-operative data set combined with the reconstructed volume image.

Following the segmentation, material properties are assigned by the processor to the segmented regions in step 5. These material properties are known or expected properties of the segmented anatomy that are provided to the processor, such as by the processor having access to an anatomical atlas. The anatomical atlas can provide a listing of relevant material properties of many different anatomical regions or organs, and the processor then selects the appropriate set of properties from the atlas that correspond to the segmented region. As noted above, the atlas can be compiled for a general patient population, or can be more specifically directed to patients comparable to the patient on whom the surgical procedure is to be implemented. For example, the atlas may be compiled from patients of the same age group as the patient, patients exhibiting the same pathological conditions of the segmented anatomy as the patient, patients having a medical history similar to that of the patient, etc.

In parallel with, or interleaved with, the aforementioned steps in accordance with the invention, in step 6 the coordinate system of the operation device (robotic manipulator) that is to be used in the procedure is brought into registration with the coordinate system of the scanning device, with which the aforementioned 3D image of the patient on the table was acquired. This registration of these coordinate systems can be implemented in any known manner, such as by knowledge of the physical relationship of the coordinate systems that results by virtue of the physical mounting of the operation device on the patient table, or by markers attached at suitable locations on the operation device that are visible in the acquired 3D data of the patient on the patient table, in which case the operation device must also be within the field of view of the scanning device. Suitable navigation systems are also known that identify the respective coordinate systems of the operation device and the scanner, and bring those coordinate systems into registration with each other.

The interventional procedure is then started, using the operation device in order to selectively manipulate anatomy or an organ within the reconstructed volume (step 7). Commercially available operation devices, such as robotic manipulators, provide haptic feedback to the surgeon who is operating the device, and for this purpose contain force sensors that detect forces that are applied to the anatomy or organ by the operation device during the course of the procedure. The processor that is used by the operation device to provide the haptic feedback thus may already provide an accurate estimate of the force or forces that are applied to the anatomy or organ during the procedure, and the output of this processor can be provided to the processor that controls display of the segmented region at a display screen situated at the operation venue, which can be seen by the surgeon during the course of the procedure.

Alternatively, the outputs of these force sensors can be directly supplied to the processor, and the processor can generate its own estimate of the force or forces that have been applied to the segmented volume.

Either type of estimation takes place in step 8.

Based on the estimated force or forces applied to the segmented volume at any given time during the procedure, and based on the material properties of the segmented regions, the processor automatically determines in step 9, modification or displacement of the organ or anatomy that has occurred, and updates the display of the segmented volume in step 10 in order to incorporate such modification or displacement. This updated segmented volume is then visualized at the display in step 11, and can be selectively manipulated by the surgeon in the usual manner of a segmented volume, such as by rotation or translation thereof.

The surgeon thus not only sees the state of the segmented anatomy or organ as it changes during the course of the procedure, but also can manipulate the updated (current) segmented volume so as to obtain views thereof that would not be available from a conventional endoscopic image, which can only detect the side of the anatomy or organ that is facing the endoscopic camera.

Figure 2:
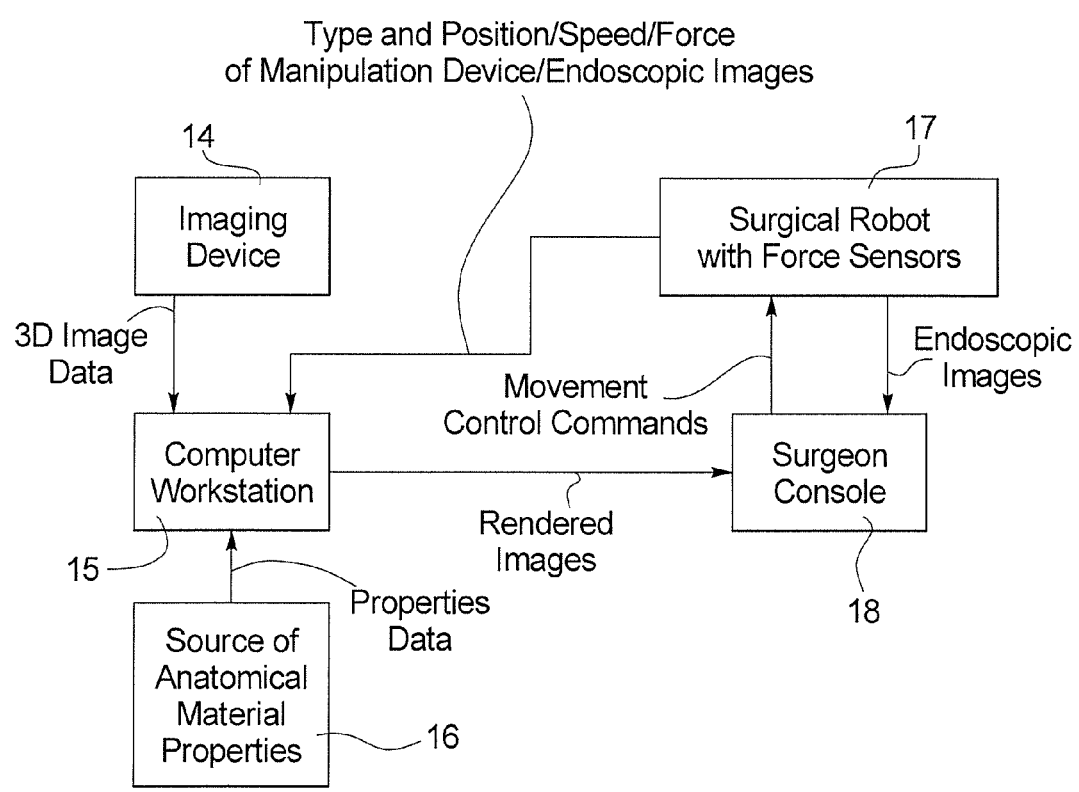
FIG. 2 is a block diagram showing the basic components of an apparatus constructed and operating in accordance with the present invention.

FIG. 2 is a block diagram illustrating the basic components of the apparatus according to the invention. The apparatus includes an imaging device or system 14, such as a C-arm x-ray imaging system mounted on a robot. Such a system may be, for example, the Artis VD 11 angio-system that is commercially available from Siemens Healthcare. The system can include suitable collision monitoring components and other control modules of the type that are conventionally available for use in a surgical environment. The imaging system 14 includes a patient table, on which the patient lies during the procedure, to which a surgical robot 17 is mounted. The surgical robot is operated from a surgeon console 18, which includes any number of control elements that are manipulated by the surgeon during the course of the procedure. The manipulations that are made by the surgeon at the console are translated to movements of the surgical robot, including the operation of tools or instruments carried by the surgical robot, such as scissors, grabbers, etc. The surgeon console provides appropriate control commands to the robot that cause the aforementioned actions to be implemented. The robot can carry an endoscopic camera having a field of view that encompasses the surgery site, so that endoscopic images of the surgery site are provided to the surgeon at the surgeon console.

The imaging system is operated by a computer at a workstation (control console) 15 to acquire the aforementioned 3D images of the patient on the table, such as CT images. The acquired 3D data are reconstructed to show an image of the acquired region, from which anatomy or an organ of interest is then segmented at the workstation 15. The aforementioned endoscopic images can also be supplied to the workstation 15, as are the forces detected by the force sensors that are present at the surgical robot 17. From this applied force information, and the aforementioned material properties of the segmented regions that are known to the processor at the workstation 15 from a source 16, the updating of the segmented regions, as described above, takes place at the workstation 15, so that the updated segmented images incorporate changes and displacements to the segmented anatomy or organ that have occurred during the course of the intervention. The updated segmented region can be displayed at a display screen of the workstation 15, which is visible by the surgeon from the surgeon console, or can be supplied to the display screen at the surgeon console 18 for display together with the endoscopic images. The updated segmented regions can be manipulated by the surgeon either via controls that are made available directly at the surgeon console, or that are available at the workstation. The surgeon may simultaneously be able to operate the workstation 15, or may provide oral directions to an assistant situated at the workstation 15 in order to manipulate the updated segmented image as the surgeon directs.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for providing current images of a surgical site during a robotically-implemented surgical procedure, comprising:
    operating a medical imaging device to acquire 3D data representing a volume of a patient situated on a patient table, said volume comprising anatomy that will be manipulated, during a surgical procedure, by a manually-operated surgical robot;
    providing said 3D data to a processor and, in said processor, reconstructing a 3D image of said volume from said 3D data;
    via said processor, segmenting a 3D volumetric image of said anatomy from said 3D image of said volume;
    in said processor, automatically determining at least one material property of said anatomy;
    in said processor, bringing a coordinate system of said surgical robot into registration with a coordinate system of said medical imaging device;
    beginning said surgical procedure and, in said surgical procedure, manually operating said surgical robot to apply at least one force to said anatomy that produces a geometrical change of said anatomy;
    providing an electronic signal representing said force to said processor and, in said processor, automatically updating the segmented volumetric image of said anatomy, based on said force and said at least one material property of said anatomy, to produce an updated segmented volumetric image of said anatomy that visually shows said change in the geometry of said anatomy; and
    at a display screen in communication with said processor, displaying said updated segmented volumetric image of said anatomy in real-time during said surgical procedure.

2. A method as claimed in claim 1 comprising storing at least one material property respectively for different anatomical objects in an electronic database, and accessing said electronic database from said processor to obtain said at least one material property from said database for said anatomy in said segmented volumetric image.

3. A method as claimed in claim 2 comprising:
    obtaining a pre-operative data set from said patient prior to acquiring said 3D dataset from the patient on the table, said preoperative data set also comprising the volume of the patient that is comprised in the 3D data set;
    providing said pre-operative data set to said processor and, in said processor, bringing pre-operative data set into registration with the image reconstructed from said 3D data set and combining said pre-operative data set with said image reconstructed from said 3D data; and
    segmenting said anatomy from said combined image to obtain said segmented volumetric image of said anatomy.

4. A method as claimed in claim 1 comprising:
    during said surgical procedure, also obtaining an endoscopic image of said anatomy and displaying said endoscopic image of said anatomy at a display screen during said surgical procedure; and
    during said surgical procedure, manipulating said updated segmented volumetric image of said anatomy to show a view of said anatomy that is not visible in said endoscopic image.

5. A method as claimed in claim 1 comprising manually segmenting said anatomy from said image of said volume reconstructed from said 3D data by manual interaction, via said processor, with said image of said volume reconstructed from said 3D data.

6. A method as claimed in claim 1 comprising automatically segmenting said anatomy in said processor from said image of said volume reconstructed from said 3D data, by executing a segmentation algorithm with pattern recognition.

7. An apparatus for providing current images of a surgical site during a robotically-implemented surgical procedure, comprising:
a surgery facility comprising a patient table adapted to receive a patient thereon, a medical imaging device, and a manually-operated surgical robot comprising at least one instrument that is manually operable during a surgical procedure, and a force sensor that detects a force applied by said at least one instrument to anatomy of the patient that is involved in said surgical procedure;
a control computer to operate said medical imaging device to acquire 3D data representing a volume of a patient situated on a patient table, said volume comprising anatomy that will be manipulated, during a surgical procedure, by a manually-operated surgical robot;
said control computer being configured to reconstruct a 3D image of said volume from said 3D data;
said processor being configured to segment a 3D volumetric image of said anatomy from said 3D image of said volume;
said processor being configured to automatically determine at least one material property of said anatomy;
said processor being configured to bring a coordinate system of said surgical robot into registration with a coordinate system of said medical imaging device;
said surgical robot being configured to allow a surgeon to implement said surgical procedure and, in said surgical procedure, manually-operate said surgical robot to apply at least one force to said anatomy that produces a geometrical change of said anatomy;
said surgical robot being configured to provide an electronic signal representing said force to said processor and said processor being configured to automatically update the segmented volumetric image of said anatomy, based on said force and said at least one material property of said anatomy, to produce an updated segmented volumetric image of said anatomy that visually shows said change in the geometry of said anatomy; and
a display screen in communication with said processor, said processor being configured to display said updated segmented volumetric image of said anatomy in real-time during said surgical procedure at said display screen.

8. An apparatus as claimed in claim 7 comprising an electronic database in which at least one material property respectively for different anatomical objects is stored, and said processor being configured to access said electronic database to obtain said at least one material property from said database for said anatomy in said segmented volumetric image.

9. An apparatus as claimed in claim 8 comprising:
a source of a pre-operative data set acquired from said patient prior to acquiring said 3D dataset from the patient on the table, said preoperative data set also comprising the volume of the patient that is comprised in the 3D data set;
said processor being configured to receive said pre-operative data set and to bring pre-operative data set into registration with the image reconstructed from said 3D data set, and combine said pre-operative data set with said image reconstructed from said 3D data; and
said processor being configured to segment said anatomy from said combined image to obtain said segmented volumetric image of said anatomy.

10. An apparatus as claimed in claim 7 comprising:
an endoscopic camera at said surgical robot, said endoscopic camera, during said surgical procedure, obtaining an endoscopic image of said anatomy and displaying said endoscopic image of said anatomy at a display screen during said surgical procedure; and
said control computer being configured to allow, during said surgical procedure, manipulating of said updated segmented volumetric image of said anatomy to show a view of said anatomy that is not visible in said endoscopic image.

11. An apparatus as claimed in claim 7 comprising a user interface configured to allow manual segmenting of said anatomy from said image of said volume reconstructed from said 3D data by manual interaction with said processor, via said interface, with said image of said volume reconstructed from said 3D data.

12. An apparatus as claimed in claim 7 wherein said processor is configured to automatically segment said anatomy in said processor from said image of said volume reconstructed from said 3D data, by executing a segmentation algorithm with pattern recognition.

13. A non-transitory, computer-readable data storage medium encoded with programming instructions, said storage medium being loaded into a computer of a surgery facility comprising a patient table adapted to receive a patient thereon, a medical imaging device, and a manually-operated surgical robot comprising at least one instrument that is manually operable during a surgical procedure, and a force sensor that detects a force applied by said at least one instrument to anatomy of the patient that is involved in said surgical procedure, said programming instructions causing said computer to:
operate said medical imaging device to acquire 3D data representing a volume of a patient situated on the patient table, said volume comprising anatomy that will be manipulated, during a surgical procedure, by a manually-operated surgical robot;
reconstruct a 3D image of said volume from said 3D data;
segment a 3D volumetric image of said anatomy from said 3D image of said volume;
automatically determine at least one material property of said anatomy;
bring a coordinate system of said surgical robot into registration with a coordinate system of said medical imaging device;
in said surgical procedure, manually-operate said surgical robot to apply at least one force to said anatomy that produces a geometrical change of said anatomy;
generate an electronic signal representing said force and, in said processor, automatically update the segmented volumetric image of said anatomy, based on said force and said at least one material property of said anatomy, to produce an updated segmented volumetric image of said anatomy that visually shows said change in the geometry of said anatomy; and at a display screen display said updated segmented volumetric image of said anatomy in real-time during said surgical procedure.

\* \* \* \* \*